United States Patent [19]

Cheeke

[11] Patent Number: 4,694,699
[45] Date of Patent: Sep. 22, 1987

[54] ACOUSTIC MICROSCOPY

[75] Inventor: John D. N. Cheeke, Sherbrooke, Canada

[73] Assignee: Universite de Sherbrooke, Sherbrooke, Canada

[21] Appl. No.: 880,664

[22] Filed: Jun. 30, 1986

[51] Int. Cl.$^4$ ............................................. G01N 29/00
[52] U.S. Cl. ...................................................... 73/606
[58] Field of Search ................................... 73/606, 642

[56] References Cited

U.S. PATENT DOCUMENTS

| | | | |
|---|---|---|---|
| 2,485,722 | 10/1949 | Erwin | 310/360 |
| 4,075,516 | 2/1978 | Hattori et al. | 310/334 |
| 4,305,014 | 12/1981 | Borburgh | 310/334 |
| 4,325,258 | 4/1982 | Foster | 73/642 |
| 4,401,910 | 8/1983 | Beerman | 73/642 |
| 4,510,810 | 4/1985 | Kanda | 73/606 |
| 4,524,621 | 6/1985 | Yamanaka | 73/597 |
| 4,541,281 | 9/1985 | Chubachi et al. | 73/606 |
| 4,603,585 | 8/1986 | Atalar | 73/606 |

OTHER PUBLICATIONS

Recent Advances in High Resolution Acoustic Microscopy, Mehrdad Nikoonahad, Contemp. Phys., 1984, vol. 25, No. 2, pp. 129-158.
Mechanically Scanned Acoustic Microscope, Noriyoshi Chubachi, Proceedings of 2nd Symposium on Ultrasonic Electronics, Tokyo 1981, Japanese Journal of Applied Physics, vol. 21 (1982) Supplemental 21-23, pp. 7-10.
The Acoustic Microscope, Calvin F. Quate.
La Microscopie Acoustique, Jacques Attal.
Ultrasonic Imaging, vol. 1, No. 1, 1979, "The Wedged Transducer-A Transducer Design for Broad Band Characteristics", Gerard A. Alphonse, RCA Laboratories, Princeton, NJ.
The Elsam Acoustic Microscope, A. Thaer, M. Hoppe, and W. J. Patzelt, Sonderdruck aus Leitz Mitteilungen für Wissenschaft u. Technik, vol. VIII, No. 3/4-1982, engl. pp. 61-67.
Scanning Acoustic Microscopy, Enlightened New Technique Gives In-Depth Material Analysis, J. David Cheeke, Canadian Research, Sep. 1985.
Ultrasonic Micro-Spectroscopy via Rayleigh Waves, N. Chubachi, Symposium on Rayleigh Wave Theory and Application, ed. E. A. Ash and E. G. S. Paige, Springer-Verlay 1985.
Weaver et al, IEEE Trans. SU-32, 302, 1985.

(List continued on next page.)

Primary Examiner—Anthony V. Ciarlante
Attorney, Agent, or Firm—Cushman, Darby & Cushman

[57] ABSTRACT

The present invention relates to a method and apparatus for providing a magnified image of a zone of a specimen. The method comprises the steps of generating acoustic waves having different frequencies and focussing on the zone the acoustic waves wherein different points on the zone receive and reflect acoustic waves having different frequencies, the frequency of a wave received by a given point being function of the position of the point in the zone. The method further comprises the steps of analyzing the reflected waves to generate signals representative of the physical structure of the zone at the points and establishing a correspondance between the signals and the positions of the points in the zone from the frequencies of the reflected waves and, forming from the signals a magnified representation on a display of the physical structure of the zone to construct an image of the zone. The invention also relates to the use of the same technique to obtain quantitative information on the acoustic properties of specimens on a microscopic scale. These properties, which include sound velocity and attenuation as a function of position, direction and frequency can be derived directly from the property of different emitted frequencies corresponding to different positions in the lens assembly. This property can also be used to obtain images for different incidence angles either independently or in any desired combination.

36 Claims, 18 Drawing Figures

OTHER PUBLICATIONS

Spectroscopic Examination of Thin Film Overlays, Lee, Tsai and Cheng IEEE Trans., SU-32,248, 1985.
Poirier Neron, Castonguay and Cheeke JAP 55,89, 1984.
G. S. Kino, Special Issue on Acoustic Imaging, Proceedings of the IEEE, 67,510, Apr. 1979.
Bertoni IEEE Trans SU-31,105, 1984.
Breazale et al, Jour. App. Phys. 48,530, 1977.
Neubauer and Dragonette, JAP, 45,618, 1974.
Mayer et al. JAP, 50, (12) 1979.
Acoustic Micro-Metrology, Rolf D. Weglein, IEEE Transactions on Sonics and Ultrasonics, vol. SU-32, No. 2, Mar. 1985.
Scanning Acoustic Microscopy Using PVDF Concave Lenses, Electronics Letters, 10th Oct. 1985, vol. 21, No. 21, pp. 990-992.

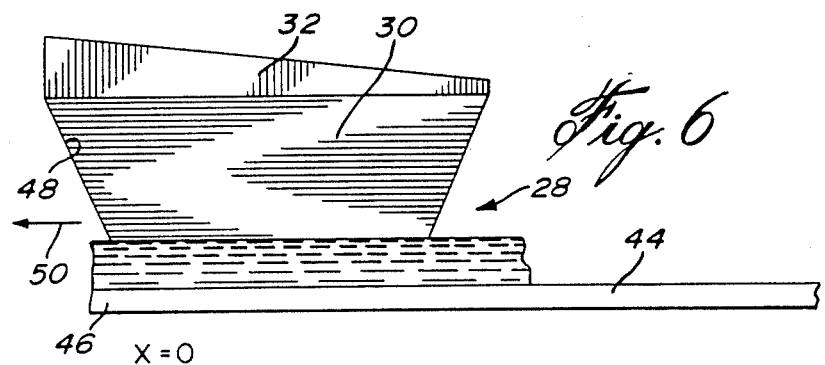
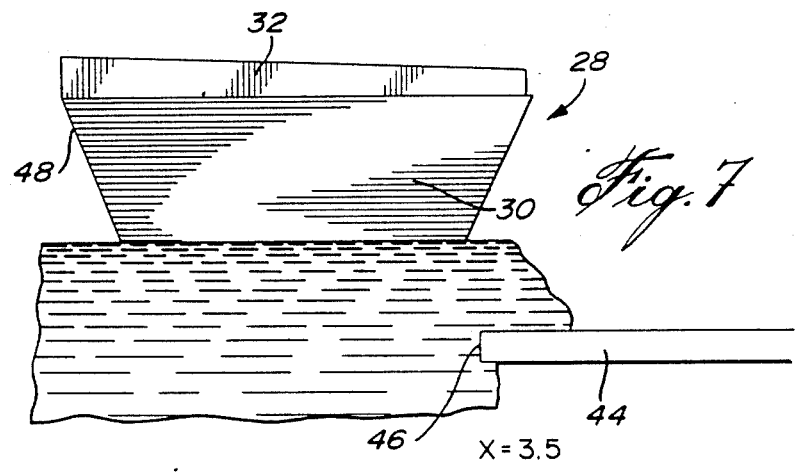
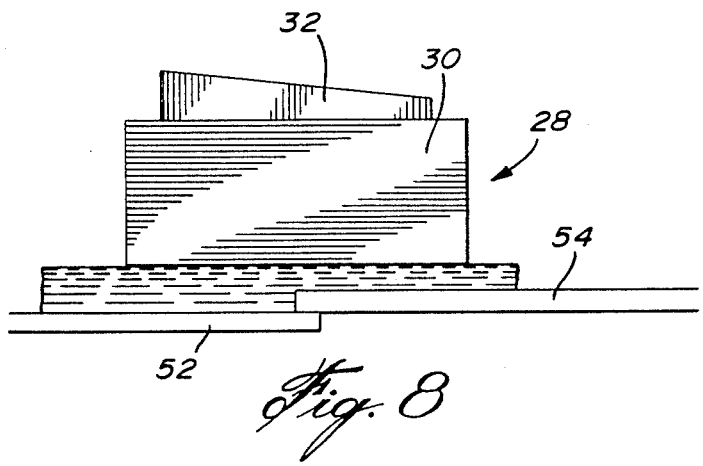

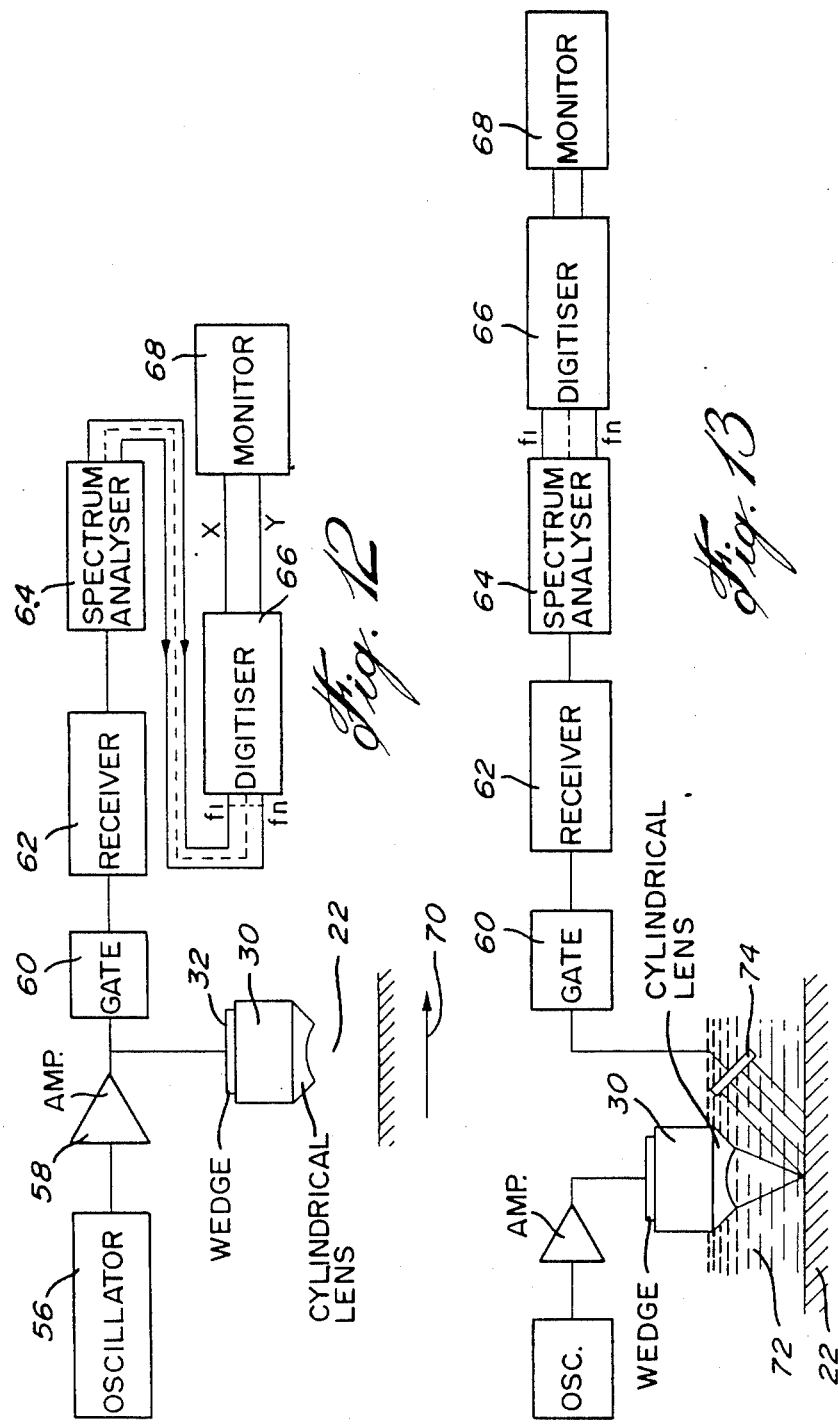

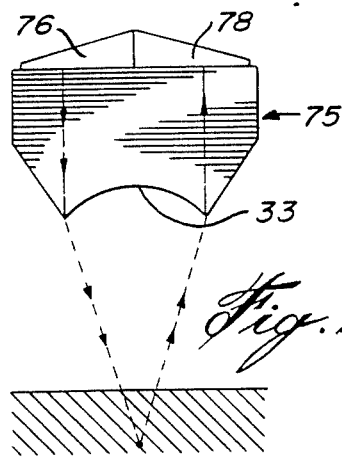
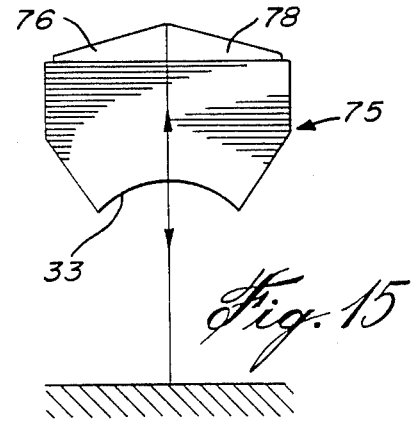
Fig. 14
Fig. 15
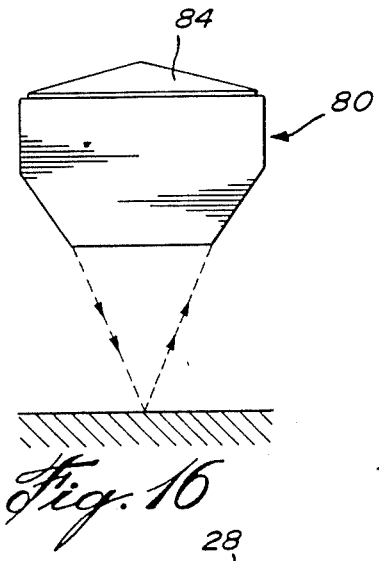
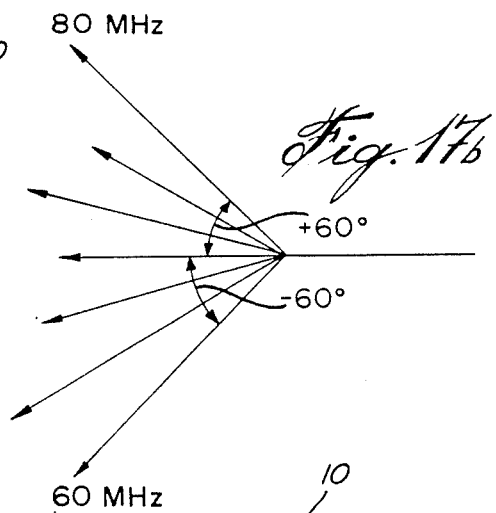
Fig. 16
Fig. 17b
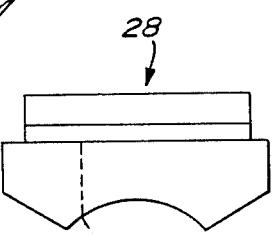
Fig. 17a

ACOUSTIC MICROSCOPY

FIELD OF THE INVENTION

The present invention relates to methods and apparatuses for the study of a specimen by an acoustic wave scanning. More specifically, the invention relates to an acoustic microscope or other systems for obtaining information about the specimen at a microscopic scale.

BACKGROUND OF THE INVENTION

Acoustic microscopy is a relatively recent technological field which was developed in the early 70's. The theory of scanning objects with ultrasonic waves is relatively simple and consists of applying microwave pulses of very short duration to a piezoelectric transducer mounted on a lens made usually of saphire or quartz. The ultrasonic waves emitted by the transducer propagate to a spherical cavity ground in the opposite face of the lens. The cavity is filled with liquid, usually water, which serves as a propagation medium between the crystal and the specimen to be studied. The ultrasonic pulse is then focussed by the cavity to a point on the specimen surface and then returned to the transducer as in the usual case of ultrasonography. The height of the reflected echo gives a measure of the local impedance and topography so that an acoustic image of the specimen can be formed by mechanically scanning the lens over the specimen's surface. This simple acoustic lens is virtually a perfect focussing element so that the actual resolving power is of the order of the wave length of the acoustic wave in the liquid.

A typical acoustic microscope operates with a resolution in the range of 1 to 10 microns in its most useful frequency range. While this is relatively modest as compared to the resolution of an optical microscope, there are several compensations. Perhaps, the most important is that ultrasonic waves can penetrate materials so subsurface details which are invisible optically can be focussed on. Also, the intrinsic contrast is much higher than in optical microscopy so no special staining techniques are required.

One major drawback of a typical acoustic microscope resides in the lengtht of time required to produce an image of a specimen. Since the ultrasonic waves are focussed on a single point, to provide an image of a given zone of the specimen situated on the surface or in depth of the specimen, the lens must be displaced step by step over the entire zone. This method, takes time and requires some mechanical means to move the lens.

Relatively recently, it has been found that useful information about a specimen can be obtained without necessarily providing an image of the specimen. This technique designated as ultrasonic microspectroscopy broadly consists of scanning the specimen with a lens which is focussed in depth of the specimen, the latter being displaced toward the lens. Only the reflected waves which appear to emanate from the focal point return to the transducer. The most important waves are those that are directly reflected near the center of the lens and a second group incident near the edge of the lens, such that the refracted waves are incident on the specimen surface at the Rayleigh angle. These waves are thus converted into Rayleigh surface waves, where they propagate along the surface and progressively re-radiate into the liquid where they are subsequently transmitted to the transducer. This group of waves interferes with the directly reflected group and it can be easily shown that the phase difference is a function of z, the specimen displacement. For large displacements a series of interference fringes is obtained. The Rayleigh wave velocity can be inferred directly from the fringe spacing and the attenuation from the decrease as a function of z.

The general variation of the power reflection coefficient (the output voltage of the lens' transducer) versus lens to specimen spacing z, often referred as a V(z) curve is characteristic of the specimen and permits to obtain Rayleigh wave velocity and attenuation information.

Most of the prior art devices performing ultrasonic micro-spectroscopy involve a mechanical displacement of the lens or the specimen with the attendant disadvantages (time consuming, high mechanical accuracy required, complicated and expensive signal analysis etc.).

OBJECTS AND STATEMENT OF THE INVENTION

An object of this invention is an improved method and apparatus for obtaining useful information about a specimen by scanning the specimen with acoustic waves.

More specifically, an object of the invention is to reduce the time necessary for obtaining the information on the specimen and to provide a simplified apparatus for scanning the specimen with acoustic waves.

Another object of the invention is an improved lens assembly for acoustic waves.

A further object of the invention is improved electric energy to acoustic energy and acoustic energy to electric energy transducers.

Hereinafter by the expression "lens assembly" will be designated a device for generating acoustic waves and for concentrating or focussing the acoustic waves on the specimen to be scanned, as well as a device for receiving acoustic waves and producing, in turn, an electric signal.

By the term "focussing" will be designated the concentration of acoustic waves on a point or a zone which is different from a point and which may be situated in depth or on the surface of the specimen.

By the term "spherical lens" will be designated an acoustic lens in which is formed a depression having the shape of a portion of a sphere.

By the term "cylindrical lens" will be designated an acoustic lens in which is formed a groove having the shape of a sector of a cylinder.

Generally speaking, the objects of this invention are achieved by creating a correspondence between the frequency of an ultrasonic wave emitted or received by the acoustic lens assembly and the position of the acoustic wave relatively to the lens assembly. In an acoustic microscope this new concept may be used to determine from the frequency of the acoustic wave the position of the point on the specimen on which the acoustic wave has been reflected.

When Rayleigh wave information is desired, acoustic waves may be emitted only at the desired position on the lens, by selecting accordingly the frequencies of the waves, for generating only Rayleigh waves in the specimen, which greatly simplifies the signal analysis of the reflected waves.

When the acoustic lens assembly is used for detecting acoustic waves instead of generating acoustic waves, the frequency-position correspondence is useful to determine the position of a reflected acoustic wave relatively to the lens assembly.

The correspondence between the position of an acoustic wave and its frequency may be advantageously used in acoustic microscopy, to obtain Rayleigh wave information, and also in a variety of other arrangements for scanning a specimen with acoustic waves, as it will be plain to a man skilled in the art.

A lens assembly in which a frequency-position correspondence is created comprises an electric energy to acoustic energy transducer mounted on a bloc of sound transmitting material for focussing the acoustic waves generated by the transducer. Different portions of the transducer generate acoustic waves having different frequencies, so that the position of an acoustic wave depends on its frequency. Similarly, when the acoustic lens assembly is used for detecting acoustic waves, it comprises an acoustic energy to electric energy transducer, different portions of the transducer being responsive to different frequencies. When an electric signal having a certain frequency is produced by the transducer, in response to an acoustic wave having the same or substantially the same frequency, it may be derived that at least that specific portion of the transducer associated with this frequency value receives the acoustic wave. Since the position of the specific portion is known and depends upon the structure of the transducer, the position of the acoustic wave relatively to the acoustic lens may be determined.

The transducer, used for detecting or generating acoustic waves preferably has a nonuniform thickness. Since the frequency of resonance of a transducer varies according to its thickness, different frequencies will be excited from portions having different thicknesses. Similarly, each portion will be responsive to a frequency value corresponding to the thickness of that portion.

The method for providing a magnified image of a specimen or a zone of a specimen when the latter is too big to be imaged in full, consists of generating preferably a packet of acoustic waves having different frequencies. The packet of waves is directed and focussed on the zone to be imaged in such a way that different points of the zone receive and reflect acoustic waves with different frequencies. The frequency of a wave reflected by a given point on the zone, corresponds to the position of the point in the zone.

Subsequently, the reflected waves are detected and analysed with an electronic circuit to form on a display such as a monitor, a magnified representation of the physical structure of the zone at the points for constructing an image of the entire zone. The representation of the physical structure at each point is formed by analyzing only the reflected wave whose frequency corresponds to the position of that point. In other words, the frequency of a wave is used to determine the position of the point from which the wave has been reflected.

As previously stated, the zone of the specimen to be imaged is not necessarily situated on the surface of the specimen. The ultrasonic waves may be focussed in depth of the specimen to provide an image of its internal physical structure. This technique is very useful when integrated circuits are inspected and an image of the silicon chip may be obtained without opening the protective capsule of the silicon chip.

According to this invention, an electronic scanning may be obtained in one direction, preferably over a narrow zone which may be assimilated to a straight line. To scan a surface, the lens assembly moves in a transverse direction while performing an electronic scanning in a longitudinal direction. The detection of the transverse position of the lens assembly can be determined by the acoustic time of flight method. In this case, the ultrasonic waves re-emitted into the liquid by the Rayleigh waves on the specimen surface are accurately time detected and digitised at high speed with high resolution so that the arrival time of a signal will be used as a measurement of its point of emission on the surface. This corresponds to a true real time surface wave image of the specimen surface, the image being typically formed in a time very much less than one second.

In one embodiment, the acoustic lens assembly for generating and focussing the ultrasonic waves on a zone corresponding to a straight line comprises a cylindrical lens made from sound transmitting material such as $Al_2O_3$. As a source of ultrasonic waves, a wedge shaped transducer is mounted on the top surface of the lens. The resonance frequency of the transducer varies inversely with the thickness of the wedge and by exciting the transducer with a signal containing a large number of spectral components, different frequencies will be excited at different positions on the transducer. The ultrasonic waves propagate through the lens and are focussed on a line on the specimen.

Different points on the line receive and reflect waves having different frequencies, the frequency of the waves varying linearly along the line. An image of the specimen at the line is constructed by forming a representation of the physical structure of the specimen at different points on the line.

With the principle according to this invention a variable aperture imaging by a combination between a conical transducer and a spherical lens, may be obtained. By exciting the transducer at the desired frequency, the emergence position of the acoustic wave on the lens may be controlled. The emergence position is electronically variable by simply adjusting the frequency. This procedure effectively produces incident waves of adjustable incidence angle in the coupling liquid between the lens assembly and the specimen. In particular, this characteristic can be used to emit acoustic waves at small incidence angles, hence at small aperture, which is desirable for subsurface imaging. One can also illuminate the lens so that Rayleigh waves are preferentially excited to obtain a surface wave image. Further, by exciting different frequencies in this way, the contrast can be varied in a continuous fashion by electronic means.

According to the present invention, Rayleigh wave information may be obtained by using a pair of wedge shaped transducers combined with a cylindrical lens. With this arrangement the lens can emit acoustic waves from the desired position on the lens so as to produce only Rayleigh waves at the surface, by one wedge and detect them by the other. In this way, Rayleigh wave velocity can be detected directly without mechanical movement and with no extra data analysis required, in contrast to the usual tedious and sophisticated methods required.

Rayleigh wave information may also be obtained by using a wedge shaped transducer and a cylindrical lens in combination with a point (spherical) lens. The point lens is used as a roughly point source of Rayleigh waves which are then detected by the wedge lens assembly. The frequency-position character of the wedge assembly means that time of flight measurement from the point source to different frequency positions can be made. This will give $V_R$(Rayleigh wave velocity) and $\alpha_R$(Rayleigh wave attenuation) as a function of direction in the specimen surface without mechanical movement. Present techniques require fabrication of a much more complex lens assembly and a mechanical displacement system for the lens or the specimen, for this measurement.

The invention comprises in a general aspect a method for obtaining information at a microscopic scale of a specimen by scanning the specimen with acoustic waves, the method comprising the steps of:

emitting acoustic waves toward the specimen by a lens assembly, the specimen reflecting the acoustic waves, the position of an acoustic wave in the lens assembly being function of the frequency of the acoustic wave;

controlling the frequency of the acoustic wave in order to control the position of the acoustic wave in the lens assembly; and detecting and analyzing the reflected acoustic waves to obtain the information.

The invention further comprehends a lens assembly for generating and focussing acoustic waves, said lens assembly comprising:

an electrical energy to acoustic energy transducer adapted to be excited by an electrical signal to generate acoustic waves, different portions of said transducer generating acoustic waves having different frequencies; and acoustic lens means operatively connected to said transducer for focussing the acoustic waves generated by the transducer.

The invention also comprises a lens assembly for detecting acoustic waves, said lens assembly comprising:

an acoustic energy to electrical energy transducer adapted to be excited by an acoustic wave to generate in response an electric signal, different portions of said transducer responding to acoustic waves having different frequencies; and acoustic lens means operatively connected to said transducer for receiving the acoustic waves.

Further, the present invention relates to a method for providing a magnified image of a zone of a specimen, the method comprising the following steps:

generating acoustic waves having different frequencies;

focussing on the zone the acoustic waves wherein different points on the zone receive and reflect acoustic waves having different frequencies, the frequencies of a wave received and reflected by a given point on the zone being function of the position of the given point in the zone; and analyzing with electronic means that reflected waves to generate signals representative of the physical structure of the zone at the points and establishing a correspondence between the signals and the positions of the points in the zone from the frequencies of the reflected waves; and forming from the signals a magnified representation on a display means of the physical structure of the zone at the points to construct a magnified image of the zone.

The invention also comprises an acoustic microscope for providing a magnified image of a zone of a specimen, the acoustic microscope comprising:

a lens assembly for generating acoustic waves having different frequencies and for focussing said acoustic waves on the zone wherein different points on the zone receive and reflect acoustic waves having different frequencies, the frequency of an acoustic wave received and reflected by a given point being function of the position of the given point in the zone; and electronic means receiving and analyzing the reflected waves to generate signals representative of the physical structure of the zone at the points and establishing a correspondence between the signals and the positions of the points in the zone from the frequencies of said reflected waves; and display means operatively connected to the electronic means for forming from the signals a magnified representation of the physical structure of the zone at the points to construct a magnified image of the zone.

The invention also comprehends a method for obtaining directional information on a specimen by scanning the specimen with acoustic waves, said method comprising the steps of:

emitting acoustic waves having a constant frequency toward said specimen wherein said waves propagate in said specimen along different directions;

detecting the acoustic waves with detector means, different portions of said detector means being responsive to acoustic waves with different frequencies, said detector means generating an output signal in response to the detection of the acoustic waves whose path leads to the portion of said detector means responsive to acoustic waves having said constant frequency;

analyzing said output signal to obtain said information.

This invention further comprises an apparatus to obtain directional information about a specimen by scanning said specimen with acoustic waves, said apparatus comprising:

means for emitting acoustic waves at constant frequency toward said specimen, said acoustic waves propagating in said specimen;

detecting means for detecting said acoustic waves, different portions of said transducer being responsive to acoustic waves having different frequencies, said detecting means generating an output signal in response to the detection of an acoustic wave whose path leads to the portion of said detecting means which is responsive to acoustic waves having said constant frequency;

analyse means for analyzing said signal to obtain said information.

DESCRIPTION OF THE DRAWINGS

FIGS. 6 and 7 are schematical views of an acoustic lens assembly according to this invention used to detect the edge of a glass slider;

FIG. 8 is a schematical view of an acoustic lens assembly according to the present invention, detecting a step formed between two glass sliders;

FIG. 12 is a block diagram of a system for scanning a specimen with acoustic waves;

FIG. 13 is a block diagram of a variant of the system shown in FIG. 13;

FIG. 14 is a schematical view of an acoustic lens assembly for obtaining Rayleigh wave information;

FIG. 15 illustrates the acoustic lens assembly of FIG. 14 emitting acoustic waves at a normal incidence angle;

FIG. 16 is a schematical view of an acoustic lens assembly using a spherical lens;

FIG. 17 is a schematical view of a system utilizing a pair of lens assemblies for obtaining Rayleigh wave information; and FIG. 17b is a schematical view illustrating the pattern of Rayleigh waves emitted in the system of FIG. 17.

DESCRIPTION OF A PRIOR ART DEVICE

Figure 1:
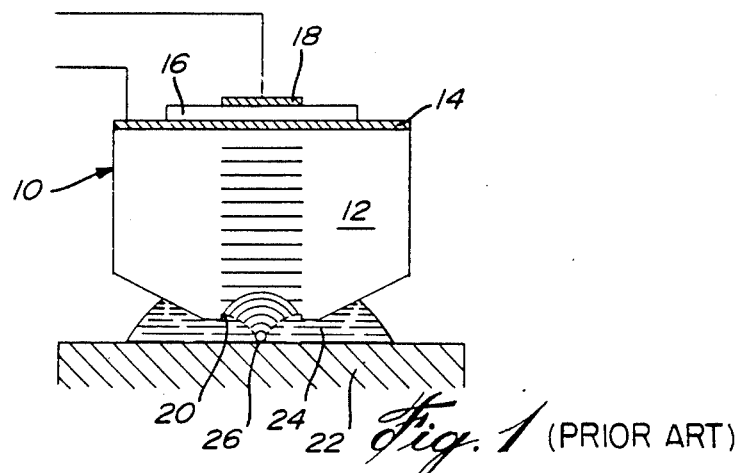
FIG. 1 is a vertical cross-sectional view of a prior art acoustic lens assembly.

A prior art spherical lens assembly 10 for an acoustic microscope is shown in FIG. 1. The lens assembly comprises a lens 12 made of a block of sound conducting material such as quartz or saphire. On the top surface of lens 12 is mounted an electrode 14 supporting a piezoelectric transducer 16 made from a zinc oxide film or a plate of LiNb0$_3$ and having an uniform thickness. On the top surface of transducer 16 is mounted a second electrode 18. On the bottom surface of block 20 is ground a semi-spherical cavity 20 which typically has a diameter of 3 mm or less.

Lens assembly 12 is positioned over a specimen 22 to be examined. A drop 24 of coupling liquid such as water adheres by capillarity to lens 12 and sample 22 and is used as a sound propagating medium from lens 12 to specimen 22.

The first step in the image-making process when the prior art lens assembly 10 is used with a conventional acoustic microscope is to convert an electrical signal into an acoustic one by means of piezoelectric transducer 16 mounted on the top surface of the lens element 12. The transducer 16 consists of many small crystals, and each crystal has a preferred direction: its long axis is usually oriented at right angles to the surface of the substrate on which it is deposited. An alternating electric field imposed along this axis by electrodes 14 and 18 will compress and expand the crystals as the polarity of the field fluctuates. Piezoelectric films of various types have been available for a number of years, and they are an integral part of many commercial acoustic devices.

The beam of ultrasound thereby generated is focussed by the acoustic lens 12 on a very small spot or point 26 in the plane of the specimen 22. The image is formed by moving the spot 26 across the specimen plane, point by point, and line by line in a raster pattern, in much the same way that the image focussed on the photosensitive surface of a television camera is recorded by scanning the surface with an electron beam. In the acoustic microscope, however, the scanning is done mechanically and the rate of scanning is much slower, which as stated earlier, constitutes a disadvantage. It takes several seconds to scan a single frame making it necessary to store the recorded signals for some time before the scan can be utilized to construct an image of the specimen.

The signals reflected from the specimen and stored in the electronic memory are finally amplified and made to modulate the intensity of the electron beam in an ordinary television receiver. The image is formed by scanning the electron beam across the screen in synchronicity with the motion of the acoustic beam across the specimen. A one-to-one correspondence is maintained between the position of the electron beam spot on the television monitor and the position of the acoustic beam spot on the specimen. If the electron beam is displaced across the television screen by one centimeter and the acoustic beam is displaced across the object by 10 micrometers, the resulting image will be magnified 1000 times. The ratio of these two displacements is easily adjusted and the images can be made to appear with magnifications ranging from 100 to several thousand times.

Figure 2:
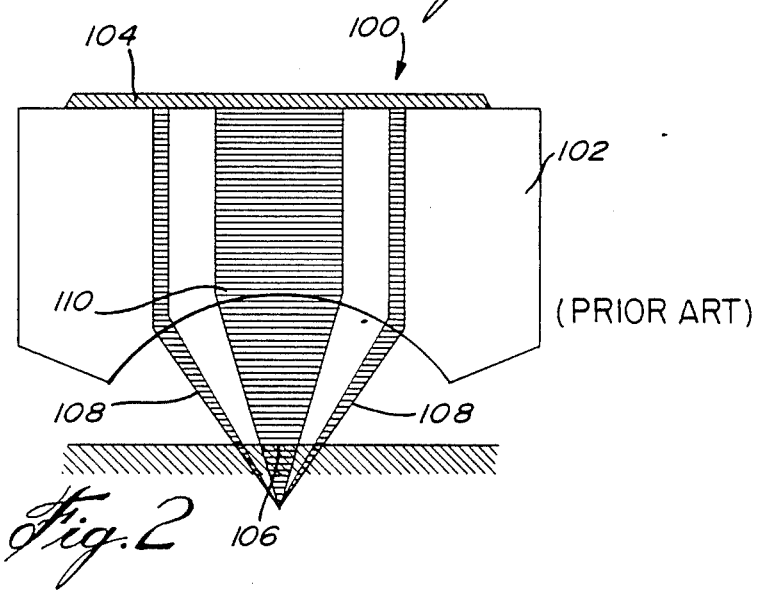
FIG. 2 is a schematical view of a prior art acoustic lens assembly used to obtain a V(z) curve of a specimen.

FIG. 2 illustrates schematically a lens assembly 100 which may be used to obtain Rayleigh wave information. Lens assembly 100 includes a spherical lens 102 supporting a transducer 104 for generating acoustic waves.

Figure 3:
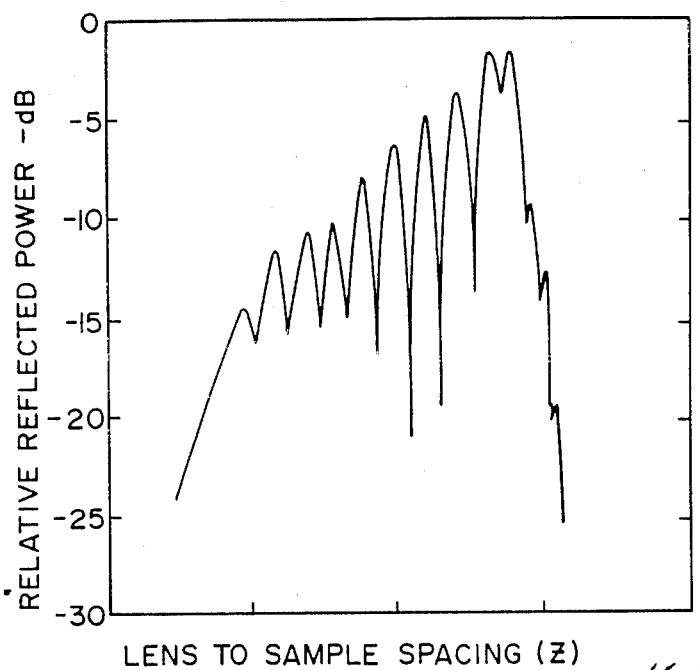
FIG. 3 illustrates a typical V(z) diagram.

Specimen 106 to be examined is displaced toward the lens 102, along the z axis, thereof. The transducer output voltage V(z) is periodic as the substrate is translated toward the lens 102. FIG. 3 illustrates a typical V(z) curve of fused SiO$_2$, measured at constant frequency of 370 MHz.

The period of the variation is characteristic of the specimen and results of the interference of two component waves 108 and 110 that are added vectorially in the transducer 104.

From the period of variation of the V(z) curve, the Rayleigh wave velocity (V$_R$) may be determined, which is characteristic of the specimen.

However, since the transducer 104 operates at a constant frequency a complex signal analysis system is necessary to distinguish from the Rayleigh waves and all the other waves generated by the transducer.

DESCRIPTION OF PREFERRED EMBODIMENTS

Figure 4:
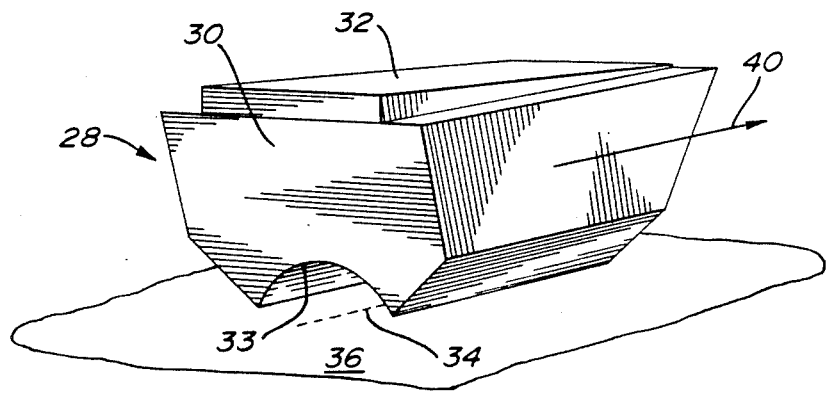
FIG. 4 is a perspective view of an acoustic lens assembly according to this invention.

With reference to FIG. 4, a cylindrical lens assembly 28 according to this invention comprises an acoustic cylindrical lens 30 made of a block of sound transmitting material such as DURALUMIN (trade mark) and a wedge shaped transducer 32 made of LiNbO$_3$, mounted on the top of lens 30. On the opposite face of cylindrical lens 30 is grounded an elongated groove 33, 1 mm wide and 3 mm long. Groove 33 extends along the direction of taper of transducer 32. Lens assembly 28 also comprises conventional electrodes (not shown) for exciting transducer 32.

Figure 5:
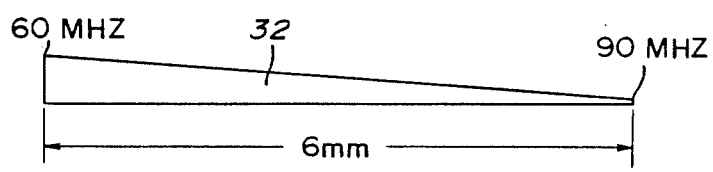
FIG. 5 is a side view of a wedge shaped transducer according to this invention.

Referring to FIG. 5, the wedge shaped transducer 32 generates acoustic waves with different frequencies and to this end it exploits the relation between the frequency of the acoustic wave and the thickness of the transducer in that the excited frequency varies inversely with the thickness of the wedge. Therefore, when transducer 32 is excited with a signal containing a large number of spectral components, different frequencies will be excited by the transducer 32, the frequency varying linearly along the X direction. For example, for a LiNbO$_3$ wedge having lenght of 6 mm and a width of 2 mm, a fundamental frequency in the range of 22 to 33 MHz could be excited. However, it is well known for planar transducers that the third harmonic gives a cleaner spectral and directivity pattern. This also holds true for the wedge transducer. Accordingly it is preferable to operate transducer 32 in the frequency range of 60 to 90 MHz.

When wedge transducer 32 is excited with electrodes of conventional construction the ultrasonic waves propagate in lens 30 and are focussed on a very narrow portion or strip 34, which may be assimilated to a straight line, on the surface 36 or the subsurface of a specimen to be examined.

Since the ultrasonic waves generated by transducer 32, have a frequency which varies along the lenght of transducer 32, each point on line 34 will receive and reflect a wave having a specific frequency which is function of the position of the point on line 34.

The embodiment illustrated in FIG. 4, permits an electronic scanning in one direction, along line 34. If an image of entire surface 36 of the specimen to be formed, lens assembly 28 must be displaced in the direction indicated by the arrow 40 in order to sweep surface 36. A conventional displacement system may be used for this purpose.

A specific example of the operation of the lens assembly 28 is shown in FIG. 6. Lens assembly 28 overlies a glass-slider 44 having an end 46 which is aligned with the extremity 48 of lens 30. Water is used as coupling liquid between lens 30 and slider 44.

Figure 9:
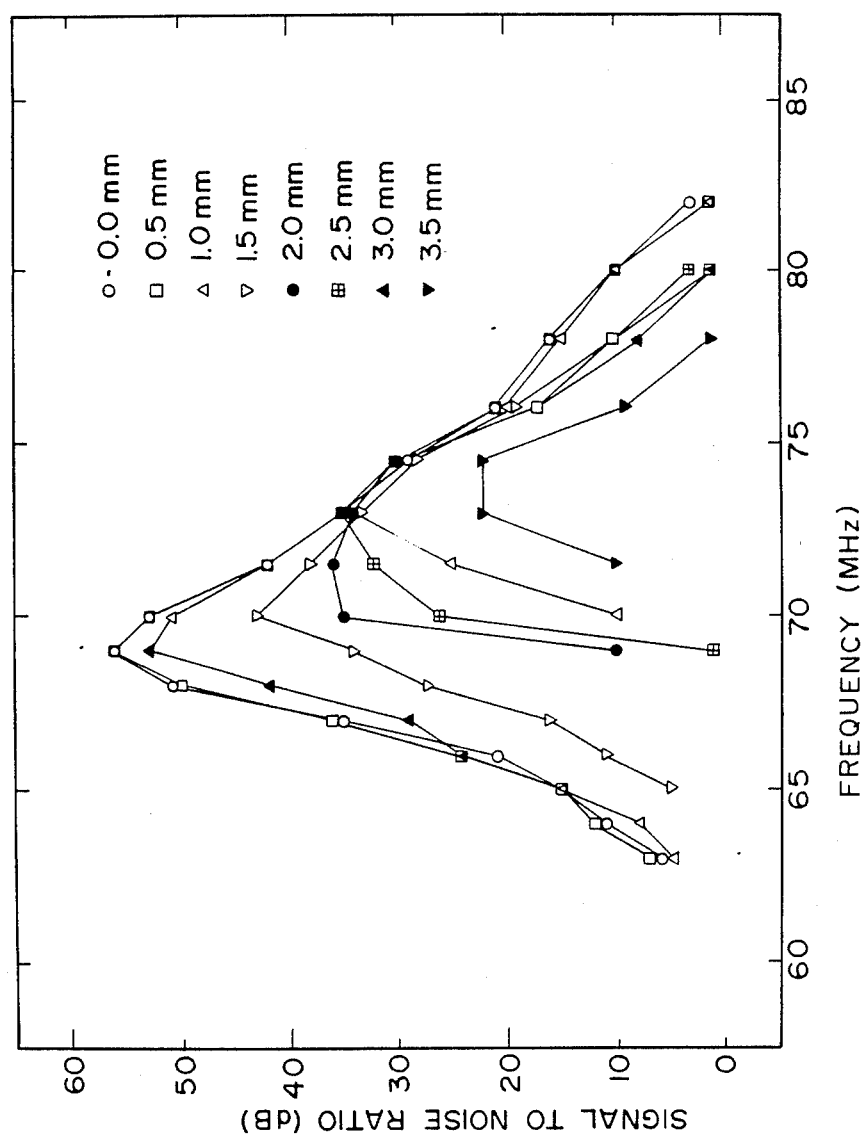
FIG. 9 is the frequency response curve of the experiment shown in FIGS. 6 and 7.

In FIG. 6, the position of slider 44 relatively to lens assembly 28 is designated as X=0. The slider is displaced to the right, in the direction indicated by arrow 50, by steps of 0.5 mm toward the position shown in FIG. 7 corresponding to X=3.5 mm. At each 0.5 mm. step, the signal noise ratio of the acoustic waves reflected from slider 44, is measured. The results are illustrated in FIG. 9. The position of the extremity 46 corresponds to a peak in the frequency response curve and it may be observed that for different positions of lens 28 relatively to the slider 44, the peak shift to the right.

Figure 10:
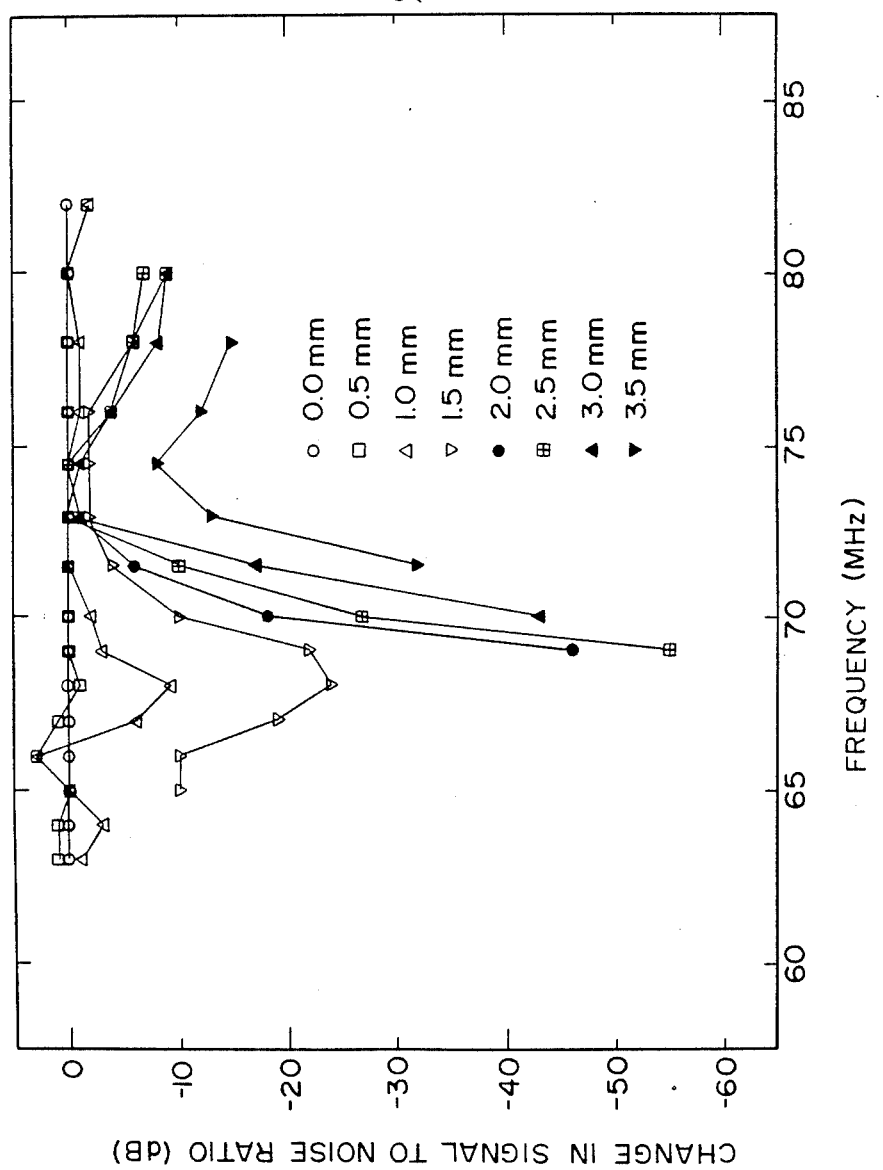
FIG. 10 is the normalized response curve of FIG. 9.

In order to obtain a clear idea of the spatial resolution, it is preferable to normalize the curves of FIG. 9 by substracting the different curves from the background at x=0. This has been done in FIG. 10 and it may be observed that the response obtained is very sensitive to small displacements in the middle of the lens.

Figure 11:
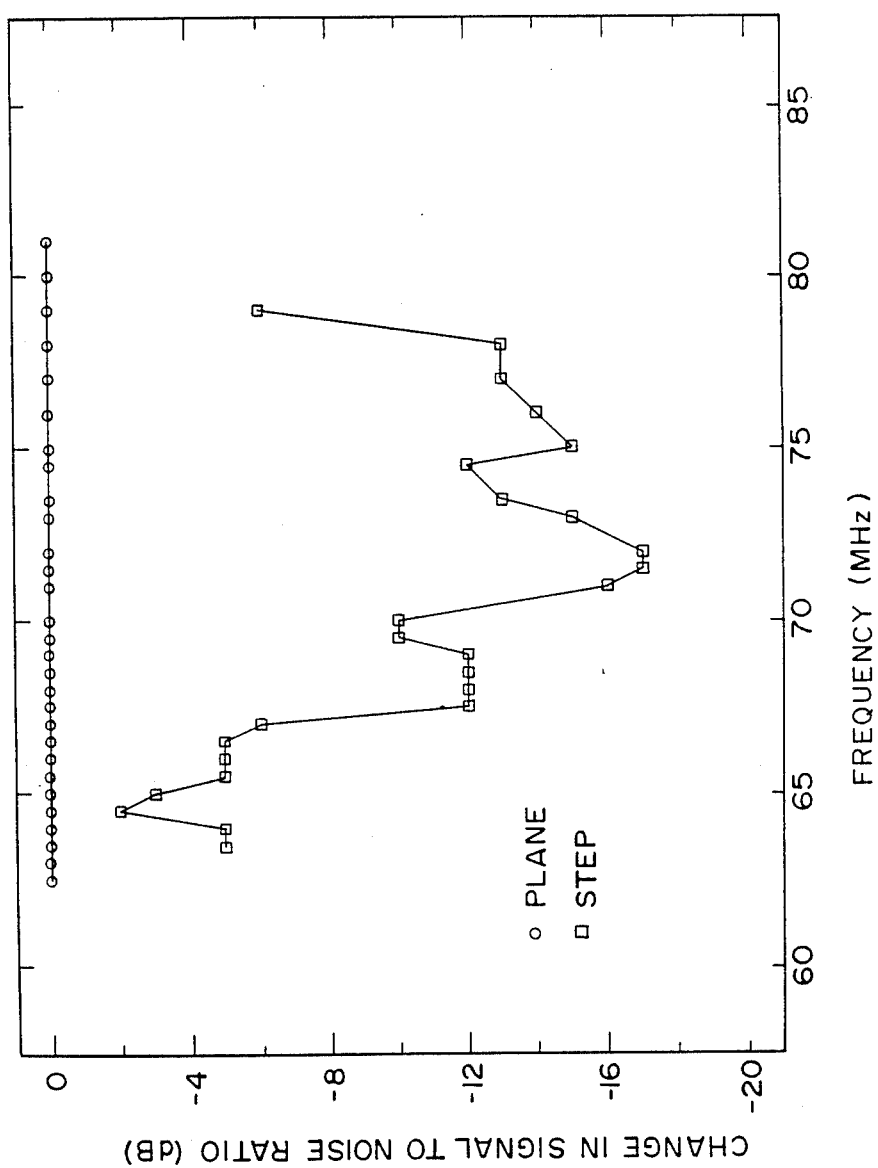
FIG. 11 is the normalized frequency response curve of the experiment shown in FIG. 8.

A second experiment is shown in FIG. 8 in which the lens assembly 28 is held in a fixed position to observe a step obtained by superposing two glass-sliders, 52 and 54 respectively. The difference curve of the frequency response is shown in FIG. 11 where the position of the step is clearly seen in the middle of the lens where it is known to be.

Lens assembly 28 may conveniently be used for obtaining an image of a zone of a specimen on a monitor. For the frequencies of the acoustic waves and from the position of lens assembly 28 relatively to the specimen, are derived X and Y deflection signals for controlling the position of the electron beam of the monitor. The intensity of the electron beam is controlled by the information conveyed by the reflected acoustic waves which have been modulated by the physical structure of the sample, for obtaining an image of the sample.

FIG. 12 illustrates a block diagram of a system for an acoustic scan which may be used for obtaining a magnified image of a specimen and utilizes a lens assembly according to this invention. An oscillator 56 generates a signal containing a large number of spectral components fed to an amplifier 58. The amplified signal is then transmitted to transducer 2 generating acoustic waves which are focussed on the specimen 22 by lens 30. The ultrasonic waves reflected from specimen 22 toward lens 30, are transmitted to wedge transducer 32 which generates in turn a waveform corresponding to the reflected acoustic waves. The waveform is separated from the signal exciting the transducer 32 by known means and is fed to a gate 60, receiver 62 and a spectrum analyzer 64. Since the output waveform of transducer 32 contains a large number of combined frequencies, each one conveying information about the physical structure of a point on specimen 22, the purpose of spectrum analyzer 64 is to separate the output waveform from transducer 32 into individual frequencies $f_1 \ldots f_n$ which are applied to a digitizer 66.

From the frequency values digitizer 66 produces an x-deflection signal for the electron beam of a monitor 68.

The transverse postion of lens 30 (direction Y, indicated by arrow 70) is determined by a known system such as the one described in the publication G. S. Kino, special issue on acoustic imaging, Proceedings of the IEEE, 67510, April, 1979. The signal of the transverse position is applied to digitizer 66, which, in turn, generates a y-deflection signal for the electron beam of monitor 68.

From the amplitude and phase of signals $f_1$ to $f_n$ is produced, in a known manner, a signal for modulating the intensity of the electron beam of monitor 68, to create a magnified image of sample 22. The information conveyed by the acoustic waves reflected from specimen 22 may also be displayed in another manner where, for example, an image of specimen 22 is not desired.

FIG. 13 illustrates a variant of a scanning system providing the coordinates of the impact positions of the acoustic waves on sample 22. The time evolution of the line focus along the specimen surface is followed by the emission of leaky waves into the coupling liquid between lens 30 and specimen 22. Such emissions have been studied by many authors both theoretically (Bertoni IEEE Trans Su-31, 105, 1984) and experimentally (Breazale et al Jour. App. Phys. 48, 530 1977, Neubauer and Dragonette, JAP 45, 618, 1974 and Mayer et al JAP, 50, (12) 1979). Neubauer et al give values of the signal loss into the liquid, which is typically 1 Neper/cm at 5 MHz and increasing linearly with the frequency.

It is proposed to monitor the emission of this wave into the coupling liquid 72 by a transducer 74 mounted as shown in FIG. 13 and digitising the detected ultrasonic pulse. The spatial address of a signal arriving at a certain time will be given by its propagation time in the water (with a correction factor for the time taken to propagate along the surface). As the longitudinal position (position along the focus line) is already known from the frequency being measured, the arrival time will thus give an (x, y) coordinate for position on the surface and the total image may be obtained electronically in a time very much less than a second.

With this configuration a surface wave image of the specimen may be obtained; the technique is most promising in the range 10-100 MHz. It may not be applicable to all specimens in a satisfactory matter due to attenuation of the surface waves and also due to complications arising from anisotropy. In these cases mechanical scanning in the transverse direction would be necessary.

The components of the system in FIG. 13, which process the output signal such as gate 60, receiver 62 etc., are of a similar nature to the ones shown in FIG. 12 and for that reason they will not be described in details here.

With reference to FIG. 14, a cylindrical lens combined with a pair of wedge-shaped transducers may be conveniently used to measure $V_r$ (Rayleigh wave velocity) and $\alpha_R$(Rayleigh wave attenuation) on the specimen's surface.

Cylindrical lens assembly 75 comprises a pair of wedge-shaped transducers 76 and 78 which taper in opposite directions and also in a direction transverse to groove 33. Lens assembly 75 extends above the specimen's surface, the focus being made in depth of the specimen. In this case a Rayleigh wave may be excited on the specimen's surface by choosing a suitable frequency to excite the sending transducer 76 spatially as shown. Similarly any desired section of the transducer can be preferentially excited to produce incidence at a certain angle on the specimen surface by chasing accordingly the frequency of the electric signal exciting the transducer.

This method permits a variety of incidence angles to be obtained. Two incidence angles are of particular interest:

(A) Normal incidence excitation

Referring to FIG. 15, the transducer is excited at low frequency hence ultrasonic waves at this frequency are emitted from the central portion of the transducer. This configuration is appropriate for;

(1) Imaging material properties;

(2) Subsurface imaging at very small aperture to reduce spherical aberration and to avoid losses due to Rayleigh wave generation (Nikoonahad, Contemporary Physics 25, 129, 1984); and (3) Spectroscopic examination of thin film overlays (Lee, Tsai and Cheng Ieee Trans. SU-32, 248, 1985).

(B) Excitation at the Rayleigh angle

With reference to FIG. 14, the excitation signal applied to the sending transducer 76 is such that the outer part of the transducer is excited so that ultrasonic waves are incident on the lens edge and are transmitted in the liquid at the Rayleigh angle. This angle will be different for each specimen and it can be controlled simply by varying the excitation frequency.

Thus, a pulse can be applied to the transducer and which will excite only a Rayleigh wave in the specimen surface. This wave will be detected by the symmetrical part of the lens on the other side and by the detecting transducer 78. The absolute value of the Rayleigh velocity can be determined by measuring the time of flight of this pulse, or for increased accuracy compare the time of flight to that in the center of the lens. The relative changes of the Rayleigh wave velocity can be measured (due to changes in propagation direction, temperature etc.) by a phase comparison method using the phase of the signal generator as a reference (Poirier Neron, Castonguay and Cheeke JAP 55, 89, 1984). Any small change in $V_R$ will then produce an interference effect with the reference.

Variable aperture imaging may be obtained with the spherical lens assembly 80 illustrated in FIG. 16. Lens assembly 80 includes a spherical lens 82 on which is mounted a conical transducer 84. As before, waves incident at any position on the lens surface may be excited to control the angle of incidence onto the specimen. Since a spherical lens is employed only ordinary mechanical scanning can be used for scanning a surface.

By appropriately choosing the frequency, an image, by either using waves at normal incidence or with Rayleigh waves, can be formed. The use of a conical transducer allows a fine tuning of the contrast which is of particular interest in materials science such as crack detection. (Weaver et al, IEEE Trans SU-32, 302, 1985).

In the configuration illustrated in FIG. 17a, a lens assembly 28 according to this invention is used in combination with a conventional spherical lens 10 so as to obtain directional information. The point beam is so designed as to maximise the amplitude of the generated Rayleigh waves. A spherical lens of small aperture with incidence at the Rayleigh angle has been found satisfactory. With this arrangement the focus of the point lens acts as a point source and Rayleigh waves are emitted in all directions (or in certain preferred directions for an anisotropic substrate.) The pattern of the emitted waves is shown in FIG. 17b. The Rayleigh waves in a given direction are then detected at the appropriate frequency. In the example shown waves at $-60$ will be detected by one end of the wedge and $+60$ by the other end (at 80 MHz). The angular range is determined by the geometry and could easily be extended by using several such assemblies disposed around a point source.

For a given direction, the following quantities can be determined:

(1) Absolute velocity, by measuring the absolute arrival time of the ultrasonic signal at a given frequency;

(2) Relative velocity by a phase comparison method with the phase of the source; and.

(3) Attenuation of the Rayleigh waves, correcting for the loss of energy by leaky wave into the liquid.

The advantages compared to previous methods include; no mechanical movement, real time, simplicity of measurement, relative intensitivity to vibrations, portability, etc.

Although the invention has been described in reference to preferred embodiments, it is to be understood that this example should not be considered as limiting in any sense except by the terms of the following claims.

The embodiments of the invention in which an exclusive property or privilege is claimed are defined as follows:

1. A method for obtaining information at a microscopic scale of a specimen by scanning said specimen with acoustic waves, said method comprising the steps of:

propagating acoustic waves of a plurality of frequencies toward said specimen, said specimen reflecting said acoustic waves, the position of a propagated acoustic wave in a reference plane which is generally perpendicular to the direction of propagation of said acoustic waves toward said specimen being a function of the frequency of the acoustic wave;

controlling the frequency of the acoustic waves in order to control the position of the propagated acoustic waves in said reference plane; and detecting and analyzing said reflected acoustic waves to obtain said information.

2. A method as defined in claim 1, wherein during the analysis of the reflected waves the frequencies thereof are measured so as to determine their respective positions in said reference plane.

3. A method as defined in claim 1, wherein said step of propagating acoustic waves includes emitting a packet of acoustic waves having different frequencies from a lens assembly, said acoustic waves being focused on said specimen, different points on said specimen receiving said reflecting acoustic waves having different frequencies.

4. A method as defined in claim 3, wherein said acoustic waves are focussed on said specimen along a line.

5. A method as defined in claim 4, wherein said acoustic lens assembly and said specimen are displaced relatively to each other, the line of focus being displaced on said specimen to sweep a zone of said specimen for obtaining information on the physical structure of said zone.

6. A method as defined in claim 5, wherein said acoustic waves are transmitted from said lens assembly to said specimen via an acoustic field medium, during the transmission of said acoustic waves leaky ultrasonic waves being emitted in said medium, said method further comprises the step of:

following the time evolution of the line of focus relatively to said specimen by measuring the propagation time of said leaky waves in said medium.

7. A method as defined in claim 1, wherein said acoustic waves are emitted at the Rayleigh angle toward said specimen so as to produce Rayleigh waves in said specimen.

8. A method as defined in claim 7, wherein said reflected waves are analyzed to determine the Rayleigh wave velocity.

9. A method as defined in claim 7, wherein said reflected waves are analyzed to determine the Rayleigh wave attenuation.

10. A method as defined in claim 1, wherein said acoustic waves are emitted at a normal incidence relatively to the surface of said specimen.

11. A lens assembly for receiving acoustic waves, said lens assembly comprising:

an acoustic energy to electrical energy transducer adapted to be excited by an acoustic wave to generate in response an electric signal, different portions of said transducer responding to acoustic waves having different frequencies; and acoustic lens means operatively connected to said transducer for receiving the acoustic waves.

12. A lens assembly for generating and focussing acoustic waves, said lens assembly comprising:

an eletrical energy to acoustic energy transducer adapted to be excited by an electrical signal to generate acoustic waves, different portions of said transducer generating acoustic waves having different frequencies; and acoustic lens means operatively connected to said transducer for focussing the acoustic waves generated by the transducer.

13. A lens assembly as defined in claim 11 or 12, wherein said transducer has a non uniform thickness.

14. A lens assembly as defined in claim 11 or 12, wherein said transducer is tapered.

15. A lens assembly as defined in claims 11 or 12, wherein said lens includes a bloc of sound transmitting material having a top face on which is mounted said transducer, said bloc including a bottom face on which is grounded an elongated groove, said transducer tapering along said groove.

16. A lens assembly as defined in claim 11 or 12, wherein said transducer has a conical shape.

17. A lens assembly as defined in claims 11 or 12, wherein said transducer has a conical shape, said lens assembly further includes a bloc of sound transmitting material having a top face on which is mounted said transducer, said bloc having a bottom face on which is formed a recess having the shape of a portion of a sphere.

18. A lens assembly for acoustic waves, said lens assembly comprising:

electric energy to acoustic energy and vice versa transducer means;

acoustic lens means comprising a top face and a bottom face in which is formed an elongated groove, said transducer means being mounted on said top face, said transducer means tapering toward two opposite edges thereof along a direction perpendicular to said groove.

19. A method for providing a magnified image of a zone of a specimen, said method comprising the following steps:

generating acoustic waves having different frequencies;

focussing on said zone said acoustic waves wherein different points on said zone receive and reflect acoustic waves having different frequencies, the frequency of a wave received and reflected by a given point on said zone being function of the position of said given point in said zone; and analyzing with electronic means said reflected waves to generate signals representative of the physical structure of said zone at said points and establishing a correspondance between said signals and the positions of said points in said zone from the frequencies of said reflected waves; and forming from said signals a magnified representation on a display means of the physical structure of said zone at said points to construct a magnified image of said zone.

20. A method as defined in claim 19, wherein said acoustic waves are focussed on a zone corresponding, substantially to a straight line.

21. A method as defined in claim 19, wherein said acoustic waves having different frequencies are emitted simultaneously as a packet.

22. A method as defined in claim 21, wherein said method further comprises the steps of:

focussing successively acoustic waves at a plurality of adjacent lines on said specimen, said specimen reflecting said acoustic waves at said lines;

analyzing the reflected waves; and forming on said display means magnified representations of the physical structure of said specimen at said successive lines, said representations appearing together on said display means.

23. An acoustic microscope for providing a magnified image of a zone of a specimen, said acoustic microscope comprising:

a lens assembly for generating acoustic waves having different frequencies and for focussing said acoustic waves on said zone wherein different points on said zone receive and reflect acoustic waves having different frequencies, the frequency of an acoustic wave received and reflected by a given point being function of the position of said given point in said zone; and electronic means receiving and analyzing said reflected waves to generate signals representative of the physical structure of said zone at said points and establishing a correspondence between said signals and the positions of said points in said zone from the frequencies of said reflected waves; and, display means operatively connected to said electronic means for forming from said signals a magnified representation of the physical structure of said zone at said point to construct a magnified image of said zone.

24. An acoustic microscope as defined in claim 23, wherein said acoustic waves are focussed on a zone corresponding substantially to a straight line.

25. An acoustic microscope as defined in claim 24, further comprising displacement means for moving said lens assembly and said specimen relatively to each other in order to focus successively said acoustic waves at a plurality of adjacent lines on said specimen, which reflect said acoustic waves at said lines and to analyze the reflected waves with said electronic means for forming on said display means magnified representations of the physical structure of said specimen at said successive lines, said representations appearing together on said display means.

26. An acoustic microscope as defined in claim 23, wherein said lens assembly includes:
   a lens made of sound transmitting material, said lens having a top surface and a bottom surface in which is ground an elongated groove;
   a transducer for generating acoustic waves, said transducer being mounted on said top surface of said lens and tapering along said groove; and
   electrode means operatively connected to said transducer for exciting said transducer wherein acoustic waves generated by said transducer propagates in said lens are focussed by said lens on said line.

27. A lens assembly to be used with an acoustic microscope, said lens assembly including:
   a lens made of sound transmitting material, said lens having a top surface and a bottom surface in which is ground an elongated groove;
   a transducer for generating acoustic waves, said transducer being mounted on the top surface of said lens and tapering along said groove; and
   electrode means operatively connected to said transducer for exciting said transducer, wherein acoustic waves generated by said transducer propagate in said lens and are focussed by said lens.

28. A method for obtaining directional information on a specimen by scanning the specimen with acoustic waves, said method comprising the steps of:
   emitting acoustic waves having a constant frequency toward said specimen wherein said waves propagate in said specimen along different directions;
   detecting the acoustic waves with detector means, different portions of said detector means being responsive to acoustic waves with different frequencies, said detector means generating an output signal in response to the detection of the acoustic waves whose path leads to the portion of said detector means responsive to acoustic waves having said constant frequency;
   analyzing said output signal to obtain said information.

29. A method as defined in claim 28, wherein said acoustic waves are Rayleigh waves.

30. A method as defined in claim 28, wherein during the analysis of said output signal said direction of travel is determined.

31. An apparatus to obtain directional information about a specimen by scanning said specimen with acoustic waves, said apparatus comprising:
   means for emitting acoustic waves at constant frequency toward said specimen, said acoustic waves propagating in said specimen;
   detecting means for detecting said acoustic waves, different portions of said transducer being responsive to acoustic waves having different frequencies, said detecting means generating an output signal in response to the detection of an acoustic wave whose path leads to the portion of said detecting means which is responsive to acoustic waves having said constant frequency;
   analyse means for analyzing said signal to obtain said information.

32. An apparatus as defined in claim 31, wherein said detecting means comprise an acoustic energy to electric energy transducer having a non uniform thickness, said transducer being operatively connected to an acoustic lens means.

33. An apparatus as defined in claim 32, wherein said transducer is tapered.

34. An apparatus as defined in claim 32, wherein said acoustic lens means comprises a bloc of sound transmitting material having a top face and a bottom face, said transducer being mounted on said top face, a groove being formed on said bottom face.

35. An apparatus as defined in claim 34, wherein said transducer tapers along said groove.

36. An apparatus as defined in claim 31, wherein said means for emitting acoustic waves include an acoustic lens assembly, generating acoustic waves having a constant frequency.

* * * * *